US012571862B2

(12) United States Patent
Kartäusch

(10) Patent No.: US 12,571,862 B2
(45) Date of Patent: Mar. 10, 2026

(54) B1 FIELD MAP WITH CONTRAST MEDIUM INJECTION

(71) Applicant: Siemens Healthcare GmbH, Erlangen (DE)

(72) Inventor: Ralf Kartäusch, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 1325 days.

(21) Appl. No.: 16/397,150

(22) Filed: Apr. 29, 2019

(65) Prior Publication Data

US 2019/0336082 A1 Nov. 7, 2019

(30) Foreign Application Priority Data

May 4, 2018 (DE) .................... 10 2018 206 950.6

(51) Int. Cl.
*G01R 33/24* (2006.01)
*A61B 5/00* (2006.01)
(Continued)

(52) U.S. Cl.
CPC .......... *G01R 33/246* (2013.01); *A61B 5/7207* (2013.01); *G01R 33/4831* (2013.01); *G01R 33/5601* (2013.01)

(58) Field of Classification Search
CPC ............ A61B 5/055; A61B 2090/3954; A61B 5/0263; A61B 5/7207; A61B 6/481; G01R 33/5601; G01R 33/246; G01R 33/5608; G01R 33/5635; G01R 33/243; G01R 33/56509; G01R 33/443; G01R 33/543;
(Continued)

(56) References Cited

U.S. PATENT DOCUMENTS

| 2004/0167395 | A1* | 8/2004 | Behrenbruch | ............ | G06T 7/30 |
| | | | | | 600/431 |
| 2010/0232667 | A1* | 9/2010 | Azar | ..................... | A61B 5/418 |
| | | | | | 600/420 |

(Continued)

FOREIGN PATENT DOCUMENTS

| DE | 602004003162 T2 | 9/2007 |
| DE | 102014215956 A1 | 2/2016 |
| DE | 102014223734 B4 | 8/2018 |

OTHER PUBLICATIONS

Castro, M. A., Yao, J., Lee, C., Pang, Y., Baker, E., Butman, J., & Thomasson, D. (Feb. 2009). Improved T1 mapping by motion correction and template based B1 correction in 3T MRI brain studies. In Medical Imaging 2009: Biomedical Applications in Molecular, Structural, and Functional Imaging. SPIE (Year: 2009).*

(Continued)

*Primary Examiner* — Keith M Raymond
*Assistant Examiner* — Johnathan Maynard
(74) *Attorney, Agent, or Firm* — Lempia Summerfield Katz LLC

(57) ABSTRACT

A method is provided for determining a movement-corrected B1 field map on contrast medium injection, wherein before the injection, a B1 field map is determined. Following the contrast medium administration, a position change is determined at the position at which the B1 field map was determined. With the position change and the B1 field map, the movement-corrected B1 field map is determined.

17 Claims, 2 Drawing Sheets

| Record MR signals in first scan | ⌐41 |
| Calculate position before contrast | ⌐42 |
| Record MR signals in second scan | ⌐43 |
| Record MR signals in third scan | ⌐44 |
| Determine position change | ⌐45 |
| Correct B1 field map | ⌐46 |
| Record MR signals in fourth scan | ⌐47 |
| Process MR signals w/ corrected B1 map | ⌐48 |

(51) Int. Cl.
    *G01R 33/483*      (2006.01)
    *G01R 33/56*       (2006.01)

(58) Field of Classification Search
    CPC ............ G01R 33/5659; G01R 33/4831; G01R
           33/563; G01R 33/56316; G01R 33/56563
    See application file for complete search history.

(56)                 References Cited

U.S. PATENT DOCUMENTS

| | | | |
|---|---|---|---|
| 2014/0039300 A1* | 2/2014 | Gjesdal | G01R 33/281 |
| | | | 600/420 |
| 2016/0059041 A1* | 3/2016 | Grodzki | A61B 5/055 |
| | | | 600/1 |
| 2016/0061922 A1* | 3/2016 | Grodzki | G01R 33/5608 |
| | | | 324/309 |
| 2016/0091591 A1* | 3/2016 | Grodzki | G01R 33/56509 |
| | | | 324/309 |
| 2016/0097830 A1* | 4/2016 | Grodzki | A61B 5/7207 |
| | | | 324/309 |
| 2016/0146908 A1* | 5/2016 | Köhler | G01R 33/5659 |
| | | | 382/131 |
| 2016/0259022 A1 | 9/2016 | Beck | |
| 2017/0027472 A1* | 2/2017 | Gdaniec | A61B 5/4869 |
| 2017/0108566 A1 | 4/2017 | Fenchel | |
| 2017/0115368 A1 | 4/2017 | Chen | |
| 2017/0322276 A1 | 11/2017 | Bhat | |
| 2018/0003787 A1 | 1/2018 | Cloos | |
| 2018/0074148 A1 | 3/2018 | Pfeuffer | |
| 2018/0217220 A1* | 8/2018 | Gulani | G01R 33/5676 |

OTHER PUBLICATIONS

Rincón, T., Menini, A., Solana, A. B., Fischer, A., Kudielka, G., & Sun, W. Free breathing Motion-Robust Cardiac B1+ mapping at 3.0 T based on DREAM. (Year: 2017).*

German Search Report for German Application No. 10 2018 206 950.6 mailed May 24, 2019.

* cited by examiner

Contrast admin.

| 25 | 27 | 26 | 28 |
|---|---|---|---|
| Scan portion before contrast | | Scan portion after contrast | MRF scan |

5th scan   Contrast admin.   3rd scan 34   31   37   32   33   35   36

| Comparison scan portion | 1st scan | | | 2nd scan | | 4th scan (e.g., MRF scan) |

Record MR signals in first scan — 41

Calculate position before contrast — 42

Record MR signals in second scan — 43

Record MR signals in third scan — 44

Determine position change — 45

Correct B1 field map — 46

Record MR signals in fourth scan — 47

Process MR signals w/ corrected B1 map — 48

B1 FIELD MAP WITH CONTRAST MEDIUM INJECTION

The present patent document claims the benefit of German Patent Application No. DE 10 2018 206 950.6, filed May 4, 2018, which is also hereby incorporated by reference.

TECHNICAL FIELD

The disclosure relates to a method for recording magnetic resonance (MR) signals from a person under examination in a MR system while contrast medium is injected into a person under examination. The associated MR system, which is configured to carry out the method, is also provided. In addition, a computer program and an electronically readable data carrier are provided.

BACKGROUND

Magnetic resonance fingerprinting (MRF) is a technology for operating quantitative imaging by MR systems. Exemplary MRF methods are described in the following publications: U.S. Patent Application Publication No. 2017/0322276 A1, U.S. Patent Application Publication No. 2017/0115368 A1, U.S. Patent Application Publication No. 2018/0003787 A1, U.S. Patent Application Publication No. 2016/0259022 A1, U.S. Patent Application Publication No. 2017/0108566 A1, and U.S. Patent Application Publication No. 2018/0074148 A1.

In MRF, for each recording, the k-space may be very rapidly scanned by a spiral trajectory. The spiral trajectory enables the raw data space to be covered sufficiently to reconstruct an image from the recording. By varying parameters (such as excitation pulse, echo time, and repetition time), a balancing resistance is avoided, and the greatest possible dynamic is generated. From the series of simulated signal processes with varying input parameters, (e.g., the T1 time, the T2 time, etc.), the signal processes which are most similar to the individual pixels are then selected. Through the selection of the time procedure and thus the input parameters, the psychological parameters are thereby also determined. In this way, physiological quantitative MR parameter maps may be generated.

An important parameter in the simulation is the trajectory of the magnetic field gradients and the high frequency (HF) pulses that are used in the signal recording. Hereby a B1 field map is a precondition for the simulation of the HF pulses. It shows what tilt angle results in a person under examination in the different regions of the test person in a spatially resolved manner for a particular HF pulse. This B1 field map is configured to be as accurate as possible. For this purpose, a B1 field map is recorded before the MRF scan. If, however, the scans involve contrast medium, the T1 time is shortened at certain locations such that a B1 determination is no longer possible. This leads, in particular, in the regions of interest with a high dynamic level thereto that they may no longer be evaluated and thus no physiological parameter maps may be generated.

SUMMARY AND DESCRIPTION

The scope of the present disclosure is defined solely by the appended claims and is not affected to any degree by the statements within this summary. The present embodiments may obviate one or more of the drawbacks or limitations in the related art.

It is an object of the present disclosure to provide that even with a contrast medium injection, the calculation of B1 field maps which provide B1 information over the whole object is possible.

According to a first aspect, a method is provided for recording MR signals from a person under examination in a MR system, wherein contrast medium is injected into the person under examination. In the method, MR signals are recorded in a first scan portion for generating a first B1 field map of the person under examination before the contrast medium administration. Furthermore, the determination of a position of the person under examination in the MR system takes place before the contrast medium administration. After the contrast medium administration, the recording of MR signals then takes place in a second scan portion whereby an acquisition of information regarding a dynamic contrast medium distribution in the person under examination is possible with the MR signals. In addition, the recording of MR signals takes place in a third scan portion for the determination of a position of the person under examination in the MR system following the administration of contrast medium which the person under examination takes during the third scan portion. Subsequently, a position change of the person under examination between the position of the person under examination before the contrast medium administration and the position of the person under examination after the contrast medium administration is determined. There follows the correction of the first B1 field map using the particular movement change in order to determine a movement-corrected B1 field map. Subsequently, MR signals are recorded in a fourth scan portion, whereby the processing of the MR signals in the fourth scan portion takes place with the movement-corrected B1 field map.

By recording the B1 field map before the contrast medium administration and the subsequent movement correction without recording a new complete B1 field map, in order to determine the movement-corrected B1 field map, it is possible also to use accurate B1 field maps for applications which use contrast medium.

The MR signals recorded in the fourth scan portion may be used to generate at least one quantitative physiological MR parameter map of the person under examination. For example, in the fourth scan portion, the recording of the MR signals takes place with the aid of the MRF technology. In the fourth scan portion, however, other methods may also be used, in which a B1 field map is necessary for evaluating the data.

During the recording of the MR signals in the third scan portion, MR profile scans may be carried out in different spatial directions, for example, in the three orthogonal spatial directions, whereby each profile scan has a projection of the MR signals of the person under examination into one of the spatial directions. The determination of the position of the person under examination following contrast medium administration may thus take place very rapidly, for example, within less than 1 second. Through the MR profile scans, the edges of the person under examination are recognizable, so that the position of the person under examination following contrast medium administration may be calculated therefrom. Thus, an accurate determination of the movement or position change is possible.

The position of the person under examination, before contrast medium administration, may be determined, for example, by recording additional MR signals in a fifth scan portion before the contrast medium administration. In the fifth scan portion, for example, MR profile scans may likewise be carried out in the different spatial directions, whereby each profile scan again has a projection of the MR signals of the person under examination into one of the spatial directions.

It is also possible to calculate the position of the person under examination before the contrast medium administration without an additional scan portion, specifically using the B1 field map calculated before the contrast medium administration. The B1 map also shows very accurately the outer contours of the person under examination so that a position of the person under examination before the contrast medium administration may be determined precisely.

From the position change of the person under examination, a transformation matrix may be calculated which is applied to the first B1 field map for determining the movement-corrected B1 field map. This transformation matrix may take account of either just translation movements or of translation and rotation movements.

The third scan portion, in which the position of the person under examination is calculated following contrast medium administration, may be recorded immediately before the fourth scan portion or during the fourth scan portion, in which the movement-corrected B1 field map is then used.

Furthermore, before the contrast medium administration, MR signals may be recorded in a comparison scan portion with at least one imaging sequence, whereby this imaging sequence corresponds to the imaging sequence that is used in the second scan portion for obtaining the dynamic contrast medium distribution.

Before and after the contrast medium administration, the same scans may hereby be carried out in order to be able to identify the difference in the MR signals after contrast medium administration.

The disclosure also relates to the MR system which is configured for the recording of the multiple signals as described above, wherein the MR system includes at least one receiving coil for recording MR signals, a control unit and a memory unit, whereby the memory unit stores control information executable by the control unit. The MR system is configured, on execution of the control information in the control unit, to carry out the method described above.

Furthermore, a computer program product is provided, with program code loadable directly into a memory unit of a control unit of the MR system in order to carry out the acts of the method described above when the program code is executed in the control unit.

An electronically readable data carrier with electronically readable control information stored thereon is also provided, which is configured such that, on use of the data carrier in the control device of the MR system, to carry out the method as described above.

The features described above and the features which are disclosed below may be used not only in the corresponding explicitly described combinations, but also in other combinations, provided it is not explicitly stated otherwise.

BRIEF DESCRIPTION OF THE DRAWINGS

The disclosure will now be described in greater detail, referring to the accompanying drawings.

DETAILED DESCRIPTION

Figures 1, 2:
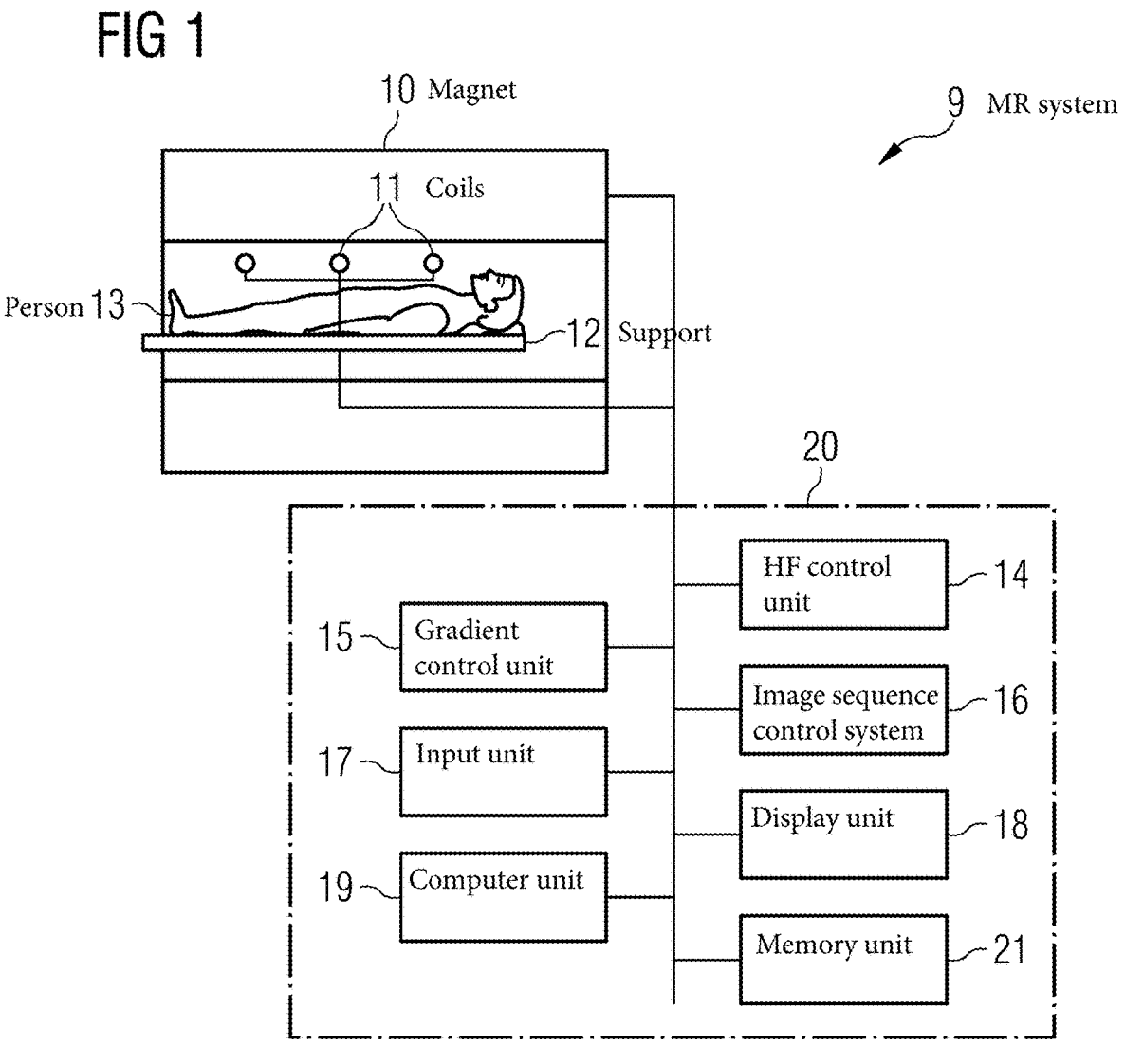
FIG. 1 depicts a schematic representation of an example of a MR system with which the B1 field maps may be calculated following contrast medium administration.
FIG. 2 depicts a schematic representation of a flow diagram with the use of a B1 map according to the prior art.

The present disclosure will now be described in greater detail based on certain embodiments, referring to the accompanying drawings. In the drawings, the same reference signs denote the same or similar elements. Furthermore, the drawings are schematic representations of different embodiments of the disclosure and the elements shown in the figures are not necessarily shown to scale. Rather, the elements shown in the drawings are reproduced so that their function and purpose are comprehensible to a person skilled in the art. The connections shown in the figures between the functional units or other elements may also be implemented as an indirect connection, whereby a connection may be wireless or wire-connected. Functional units may be implemented as hardware, software or a combination of hardware and software.

Shown schematically in FIG. 1 is a MR system with which, as described below, MR images of a person under examination 13 may be recorded, with contrast medium administration and determination of an accurate B1 field map.

The MR system 9 has a magnet 10 for generating a polarization field B0 wherein a person under examination 13 arranged on a support 12 is moved into the magnet 10 in order to record magnetic resonance signals from the person under examination 13 there. The coils 11 used for the signal recording represent the whole-body coil or the local coils that are utilized. By irradiation of high frequency (HF) pulses and the switching of magnetic field gradients, the magnetization created by the polarization field B0 may be deflected out of the equilibrium position and positionally encoded and the resultant magnetization is detected by the receiving coils 11. How MR images may be generated by the irradiation of the HF pulses and by switching magnetic field gradients in different combinations and sequences is in principle known to persons skilled in the art and is not described in detail here.

The MR system also has a control unit 20 which may be used for controlling the MR system 9. The control unit 20 has a high frequency (HF) control unit 14 and a gradient control unit 15 for controlling and switching the magnetic field gradient, wherein the HF control unit 14 is provided for the control and generation of the HF pulses for deflecting the magnetization. An image sequence control system 16 controls the sequence of the magnetic field gradients, the signal detection, and the HF pulses. By an input unit 17, an operator may control the MR system and on a display unit 18, the MR images or other information necessary for the control may be displayed. A computer unit 19 with at least one processor unit is provided for controlling the different units in the control unit 20. Furthermore, a memory unit 21 is provided in which, for example, program modules or programs may be stored which, when they are executed by the computer unit 19, may control the sequence of the MR system. The computer unit 19 may be configured, as described below, to create a movement-corrected B1 map following a contrast medium injection.

FIG. 2 depicts schematically a sequence according to the prior art wherein the generated B1 field map has not provided satisfactory results in the whole person under examination 13 because the T1 time is partially shortened such that a B1 determination is no longer possible. In a scan portion 25, the recording of MR signals takes place before the contrast medium administration, and in a scan portion 26 following the contrast medium administration in portion 27, the repetition of the same scan takes place in order to receive information about the contrast medium progress in the person under examination 13. Subsequently, in a portion 28, there follows the actual MRF scan for the determination of the quantitative physiological MR parameters such as the T1 time, the T2 time or the proton density.

In the portion 28 the recording of the MR signals for determining a B1 field map likewise takes place. In a method of this type, the contrast medium administration has shortened the T1 time to the extent that a scan of the B1 map is not possible in all regions of the person under examination 13.

Figure 3:
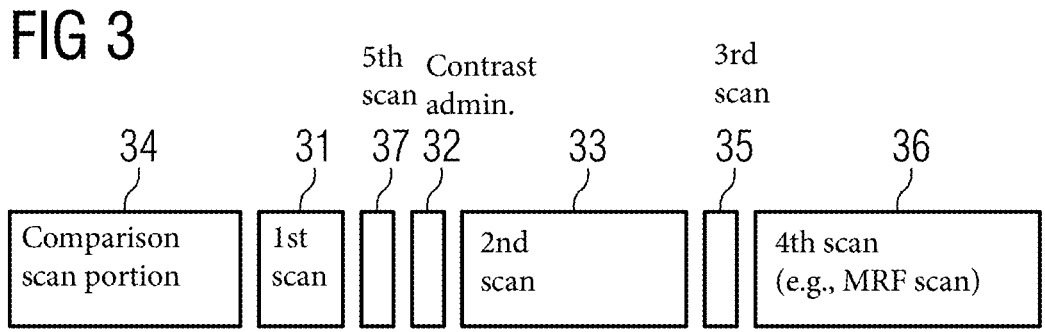
FIG. 3 depicts an example of a flow diagram for the recording of MR signals with a contrast medium injection and the calculation of a movement-corrected B1 field map.

FIG. 3 depicts a scan sequence, showing how with contrast medium injection a B1 field map may nevertheless be calculated. In a first scan portion 31, the recording of MR signals takes place for generating a first B1 field map of the person under examination 13 before the contrast medium administration. How a B1 field map may be generated with the aid of MR signals is known to a person skilled in the art. For example, an equilibrium state at different repetition times TR is used, whereby this method places the signal in relation to both the repetition times, which depends on the tilt angle and thus enables the calculation of B1. Other methods for determining the B1 map are however known, but all the known methods may be used here. Finally, in a portion 32, the contrast medium administration takes place. Following the contrast medium administration in portion 32, a second scan portion 33 takes place for the reception of MR signals, in order to obtain information about the contrast medium distribution in the person under examination 13. Herein, in the second scan portion 33, the same image sequence may be used as in a comparison scan portion 34 which is carried out before the contrast medium administration. By comparison of the MR signals in the scan portions 33 and 34, the contrast medium distribution in the person under examination 13 may be determined. In the portions 33 and 34, different MR scans may be carried out, for example, fluid-attenuated scans or other scans. The imaging sequences may be the same in the scan portions 33 and 34. Following the second scan portion 33, in a third scan portion 35, the recording of MR signals for the determination of the position of the person under examination 13 in the MR system following contrast medium administration takes place. Subsequently, immediately thereafter, there follows the recording of the MR signals in the fourth scan portion 36, which is, for example, a MRF scan.

For the determination of a position change between the first scan portion 31 in which the B1 field map has been calculated before the contrast medium administration, in a fifth scan portion 37, the position of the person under examination 13 before the contrast medium administration may be determined. In the scan portions 35 and 37, profiles may be recorded along the three spatial directions. The fifth scan portion 37 may be omitted if the position of the person under examination 13 may be directly estimated from the calculated B1 field map before the contrast medium administration.

The B1 map recorded before the contrast medium administration during the first scan portion 31 has a temporal spacing from the fourth scan portion 36 which may lie in the region of several minutes. For this reason, the B1 field map calculated in portion 31 no longer fits to the scans in portion 36, due to the movements of the test person. In order to provide the accuracy of the B1 field map before the recording of the MR signals in the fourth scan portion, MR signals such as profile scans are recorded along the three spatial directions. These may be recorded within 1 second. Because the B1 map may cover the whole object, the B1 map may have a sharply defined edge. The profiles along the three spatial directions then show the change of the position of the person under examination 13 due to the movement, whereby with the changes, the B1 field map, which was recorded in the portion 31, may be corrected. With the aid of the MR signals in the portion 35, it is thus possible to generate a movement-corrected B1 field map which may then be used for post-processing the MR signals of the scan portion 36. The recording of the MR signals in the third scan portion 35 may also lie temporally within the fourth scan portion 36.

With the sequence as set out in FIG. 3, it is possible, independently of the contrast medium administration, to cover T1 and T2 maps with a large value region. The movement-corrected B1 field map may be generated because the time point of the acquisition of the B1 field map is configured to the contrast medium administration. In order to enable the correct allocation, a movement correction is used in the largest possible recording region of the person under examination 13 in order to enable the transformation of the B1 field map to the movement-corrected B1 field map.

Figure 4:
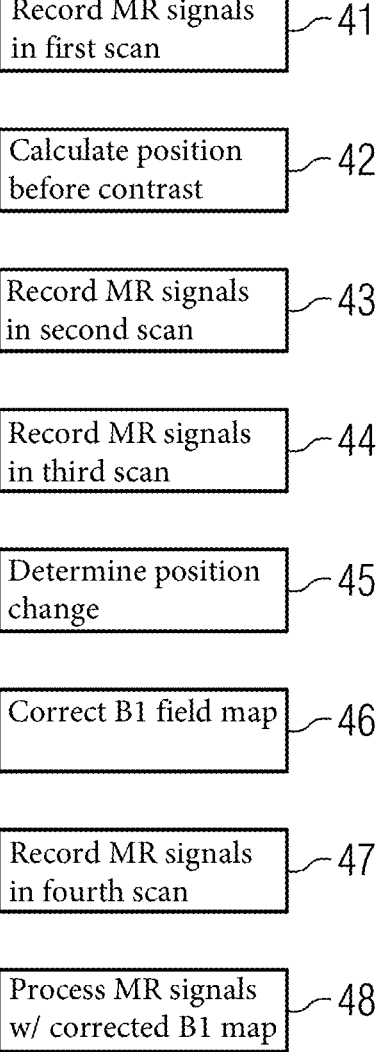
FIG. 4 depicts a schematic representation of an example of a flow diagram with the acts that may be carried out for determining a B1 field map during the use of contrast medium.

FIG. 4 brings together some acts of the method described above. In act 41, the recording of the MR signals takes place in the first scan portion 31 for generating the first B1 field map of the person under examination 13 before the contrast medium administration. Following the contrast medium administration in the portion 32, the position of the person under examination 13 in the MR system may be calculated before the contrast medium administration in the act 42. This act 42 is not necessarily completed before the contrast medium administration but may also take place thereafter during the determination of the movement-corrected B1 field map. In act 43, the recording of the MR signals takes place in the second scan portion 33 in order to follow the contrast medium distribution in the person under examination 13. In act 44, MR signals are recorded in the third scan portion 35 in order to determine the position of the person under examination 13 in the MR system after contrast medium administration. This may be achieved, for example, by profile scans or other scans which enable a determination of the position of the person under examination 13 in the MR system. In act 45, the determination of the position change of the person under examination 13 between the position before the contrast medium administration and the position after the contrast medium administration takes place. Thus, in act 46, it is possible to correct the first B1 field map that was recorded and determined in act 41 for the determination of the movement-corrected B1 field map. In act 47, the recording of the MR signals takes place in the fourth scan portion 36, for example, to determine the physiological quantitative MR parameter maps, for example, a MRF scan. In act 48, the processing of the MR signals of the fourth scan portion with the movement-corrected B1 field map takes place, so that it is possible finally to determine the quantitative physiological MR parameter maps with a high degree of accuracy.

Although the disclosure has been illustrated and described in detail by the exemplary embodiments, the disclosure is not restricted by the disclosed examples and the person skilled in the art may derive other variations from this without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for recording magnetic resonance (MR) signals from a person under examination in a MR system, wherein a contrast medium is injected into the person under examination, the method comprising:

recording MR signals in a first scan portion for generating a single, first B1 field map of the person under examination before contrast medium administration;

determining a position of the person under examination in the MR system before the contrast medium administration;

recording MR signals of the person under examination in a second scan portion after the contrast medium administration, with which a dynamic contrast medium distribution in the person under examination is configured to be acquired;

recording MR signals in a third scan portion for determination of a position of the person under examination in the MR system after the contrast medium administration received by the person under examination during the third scan portion;

determining a position change of the person under examination between the position of the person under examination before the contrast medium administration and the position of the person under examination after the contrast medium administration;

transforming the first B1 field map using the determined position change of the person under examination to provide a single person-specific movement-corrected B1 field map;

recording MR signals of the person under examination in a fourth scan portion; and processing the MR signals of the fourth scan portion using the person-specific movement-corrected B1 field map.

2. The method of claim 1, further comprising:

generating at least one quantitative physiological MR parameter map of the person under examination using the processed MR signals of the fourth scan portion.

3. The method of claim 2, wherein, during the recording of the MR signals in the third scan portion, MR profile scans are carried out in different spatial directions, wherein each MR profile scan has a projection of the MR signals of the person under examination into one spatial direction of the different spatial directions.

4. The method of claim 3, wherein the position of the person under examination before the contrast medium administration is determined based on the first B1 field map of the person under examination, and wherein the position change of the person under examination is determined from a difference of the position of the person under examination before and after the contrast medium administration.

5. The method of claim 1, wherein, during the recording of the MR signals in the third scan portion, MR profile scans are carried out in different spatial directions, wherein each MR profile scan has a projection of the MR signals of the person under examination into one spatial direction of the different spatial directions.

6. The method of claim 1, further comprising:

recording MR signals in a fifth scan portion before the contrast medium administration for the determination of the position of the person under examination in the MR system before the contrast medium administration, wherein the position change of the person under examination is determined from a position difference of the position of the person under examination before and after the contrast medium administration.

7. The method of claim 6, wherein, in the fifth scan portion, MR profile scans are carried out in different spatial directions, and wherein each profile scan has a projection of the MR signals of the person under examination into one spatial direction of the different spatial directions.

8. The method of claim 1, wherein the position of the person under examination before the contrast medium administration is determined based on the first B1 field map of the person under examination, and wherein the position change of the person under examination is determined from a difference of the position of the person under examination before and after the contrast medium administration.

9. The method of claim 1, further comprising:

determining a transformation matrix from the position change of the person under examination, wherein the transformation matrix is applied to the first B1 field map for determining the movement-corrected B1 field map.

10. The method of claim 1, wherein the third scan portion is recorded immediately before the fourth scan portion or during the fourth scan portion.

11. The method of claim 1, further comprising:

recording MR signals, before the contrast medium administration, in a comparison scan portion with at least one imaging sequence corresponding to an imaging sequence used in the second scan portion for obtaining the dynamic contrast medium distribution.

12. A magnetic resonance (MR) system configured to record MR signals from a person under examination, wherein a contrast medium is configured to be injected into the person under examination, wherein the MR system comprises at least one receiving coil for recording MR signals, a control unit, and a memory unit, wherein the memory unit stores control information items executable by the control unit, and wherein the MR system, on execution of the control information items in the control unit, is configured to:

record MR signals in a first scan portion for generating a single, first B1 field map of the person under examination before contrast medium administration, determine a position of the person under examination in the MR system before the contrast medium administration, record MR signals of the person under examination in a second scan portion after the contrast medium administration, with which a dynamic contrast medium distribution in the person under examination is configured to be acquired;

record MR signals in a third scan portion for the determination of a position of the person under examination in the MR system after the contrast medium administration received by the person under examination takes during the third scan portion;

determine a position change of the person under examination between the position of the person under examination before the contrast medium administration and the position of the person under examination after the contrast medium administration;

transform the first B1 field map using the determined position change of the person under examination to provide a single person-specific movement-corrected B1 field map;

record MR signals of the person under examination in a fourth scan portion; and process the MR signals of the fourth scan portion with the person-specific movement-corrected B1 field map.

13. The MR system of claim 12, wherein the MR system, on execution of the control information in the control unit, is further configured to:

record MR signals in a fifth scan portion before the contrast medium administration for the determination of the position of the person under examination in the MR system before the contrast medium administration, wherein the position change of the person under examination is determined from a position difference of the position of the person under examination before and after the contrast medium administration.

14. The MR system of claim 12, wherein the MR system, on execution of the control information in the control unit, is further configured to:

determine a transformation matrix from the position change of the person under examination, wherein the transformation matrix is applied to the first B1 field map for determining the movement-corrected B1 field map.

15. The MR system of claim 12, wherein the MR system, on execution of the control information in the control unit, is further configured to:

record MR signals, before the contrast medium administration, in a comparison scan portion with at least one imaging sequence corresponding to an imaging sequence used in the second scan portion for obtaining the dynamic contrast medium distribution.

16. A computer program product comprising program code, wherein the computer program product is directly loadable into a memory unit of a control unit of a magnetic resonance (MR) system, wherein the computer program product, when executed in the control unit, is configured to cause the MR system to:

record MR signals in a first scan portion for generating a single, first B1 field map of a person under examination before contrast medium administration, determine a position of the person under examination in the MR system before the contrast medium administration, record MR signals of the person under examination in a second scan portion after the contrast medium administration, with which a dynamic contrast medium distribution in the person under examination is configured to be acquired;

record MR signals in a third scan portion for the determination of a position of the person under examination in the MR system after the contrast medium administration received by the person under examination takes during the third scan portion;

determine a position change of the person under examination between the position of the person under examination before the contrast medium administration and the position of the person under examination after the contrast medium administration;

transform the first B1 field map using the determined position change of the person under examination to provide a single person-specific movement-corrected B1 field map;

record MR signals of the person under examination in a fourth scan portion; and process the MR signals of the fourth scan portion with the person-specific movement-corrected B1 field map.

17. The method of claim 2, wherein the recording of the MR signals in the fourth scan portion comprises a MR fingerprinting (MRF) scan.

* * * * *